United States Patent

(12) United States Patent
Kaggie et al.

(10) Patent No.: US 9,451,917 B2
(45) Date of Patent: Sep. 27, 2016

(54) 3T SODIUM AND PROTON COMPOSITE ARRAY FOR MAGNETIC RESONANCE IMAGING

(71) Applicant: UNIVERSITY OF UTAH RESEARCH FOUNDATION, Salt Lake City, UT (US)

(72) Inventors: Joshua D. Kaggie, West Jordan, UT (US); J. Rock Hadley, Centerville, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 14/247,125

(22) Filed: Apr. 7, 2014

(65) Prior Publication Data

US 2015/0362569 A1 Dec. 17, 2015

Related U.S. Application Data

(60) Provisional application No. 61/809,163, filed on Apr. 5, 2013.

(51) Int. Cl.
*G01R 33/14* (2006.01)
*A61B 5/00* (2006.01)
*A61B 5/055* (2006.01)
*G01R 33/3415* (2006.01)
*G01R 33/36* (2006.01)

(52) U.S. Cl.
CPC ............ *A61B 5/4312* (2013.01); *A61B 5/055* (2013.01); *G01R 33/3415* (2013.01); *G01R 33/3635* (2013.01)

(58) Field of Classification Search
CPC . A61B 5/4312; A61B 5/055; G01R 33/3415
See application file for complete search history.

(56) References Cited

U.S. PATENT DOCUMENTS

| 4,793,356 A * | 12/1988 | Misic ................. G01R 33/3628 324/318 |
| 6,414,488 B1 | 7/2002 | Chmielewski | |
| 2002/0130661 A1* | 9/2002 | Raftery ................ G01R 33/307 324/318 |
| 2002/0169374 A1* | 11/2002 | Jevtic ................... G01R 33/365 600/422 |
| 2010/0039113 A1* | 2/2010 | Vartiovaara ........ G01R 33/3657 324/322 |
| 2013/0314088 A1* | 11/2013 | Wiggins ........... G01R 33/34092 324/322 |

OTHER PUBLICATIONS

U.S. Appl. No. 61/809,163, filed Apr. 5, 2013, Kaggie (U. of Utah Res. Found).
Ballon, et al., "A 64 MHz Half-Birdcage Resonator for Clinical Imaging," J. Magnetic Resonance, vol. 90, pp. 131-140 (1990).

(Continued)

*Primary Examiner* — Daniel Miller
(74) *Attorney, Agent, or Firm* — Ballard Spahr LLP

(57) ABSTRACT

The present invention is a dual resonant breast coil design for combined sodium and proton breast MRI with increased SNR at 3T when compared to a coil with a single proton and sodium channel. The coil consists of a 7-channel sodium receive phased array, a large sodium transmit coil, and a 4-channel hydrogen transceive array. An interleaved overlapping coil layout is used to reduce coupling between sodium and proton coil elements. The new composite array coil demonstrates a 2-5× improvement in SNR for sodium imaging when compared to a simple single-loop dual resonant design.

17 Claims, 10 Drawing Sheets

(56) References Cited

OTHER PUBLICATIONS

Bangerter, et al., "Sodium MRI radiofrequency coils for body imaging," NMR Biomed. 2016; 29: 107-118.

Brown, et al., "A Flexible Nested Sodium and Proton Coil Array with Wideband Matching for Knee Cartilage MRI at 3T," Magnetic Resonance in Medicine (2015) (10 pages).

Brown, et al., "Bilateral Breast Imaging using Split-Symmetric Parallel Transmission," Proc. Intl. Soc. Mag. Reson. Med. 22 (2014).

Brown, et al., "Design of a Nested Eight-Channel Sodium and Four-Channel Proton Coil for 7T Knee Imaging," Magnetic Resonance in Medicine 70:259-268 (2013).

Brown, et al., "Design of a Nested Sodium and Proton Array for 7 Tesla Knee Imaging," Proc. Intl. Soc. Mag. Reson. Med. 20 (2012).

Chen, et al., "Quadrature Detection Coils—A Further Root-of-2 Improvement in Sensitivity," J. Magnetic Resonance, vol. 54, pp. 324-327 (1983).

Hayes, et al., "An Efficient, Highly Homogeneous Radiofrequency Coil for Whole-Body NMR Imaging at 1.5 T," J. Magnetic Resonance, vol. 63, pp. 622-628 (1985).

Lufkin, et al., "Solenoid Surface Coils in Magnetic Resonance Imaging,"AJR:146, Feb. 1986 (4 pages).

Shajan, et al., "Three-layered Radio Frequency Coil Arrangement for Sodium MRI of the Human Brain at 9.4 Tesla," Magnetic Resonance in Medicine 75:906-916 (2016).

Wiggins, et al., "High-performance radiofrequency coils for 23Na MRI: brain and musculoskeletal applications," NMR Biomed. 2016; 29: 96-106.

\* cited by examiner

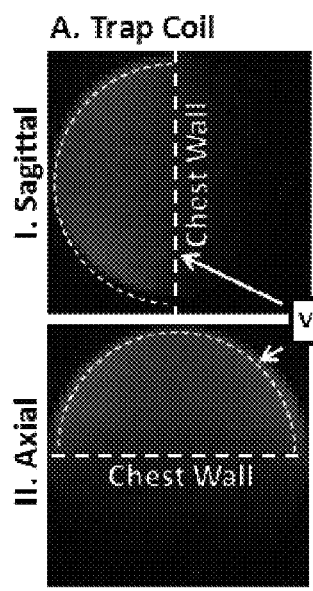
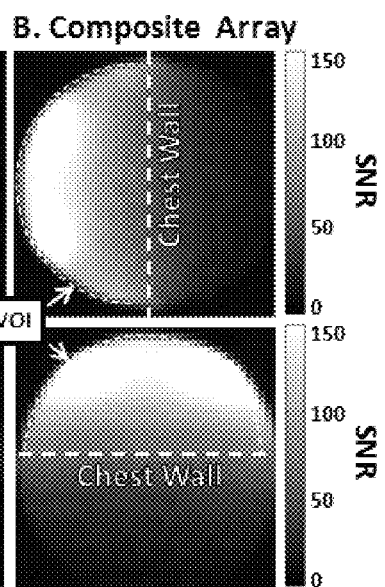
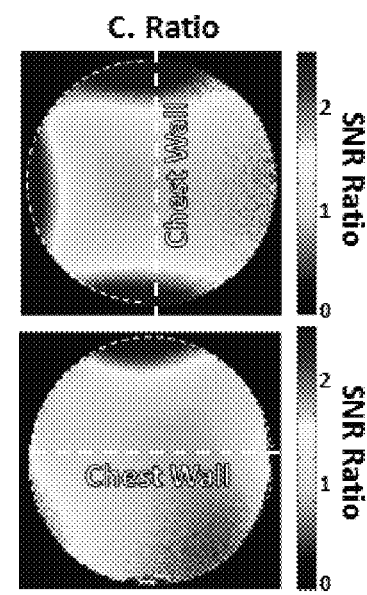
FIG. 15A   FIG. 15B   FIG. 15C
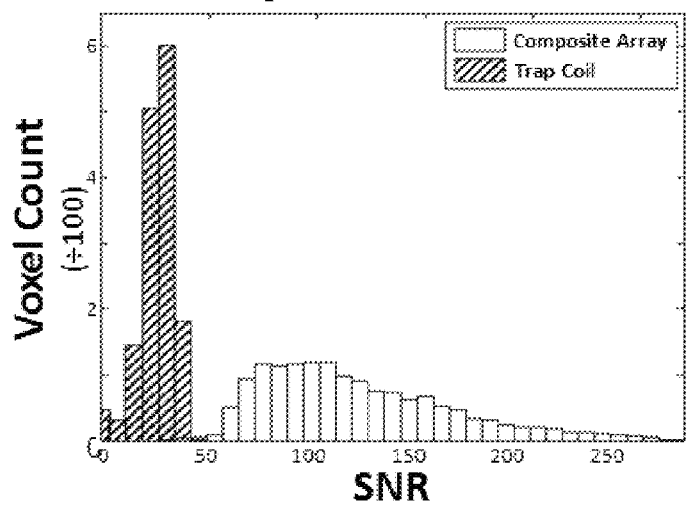
FIG. 15D

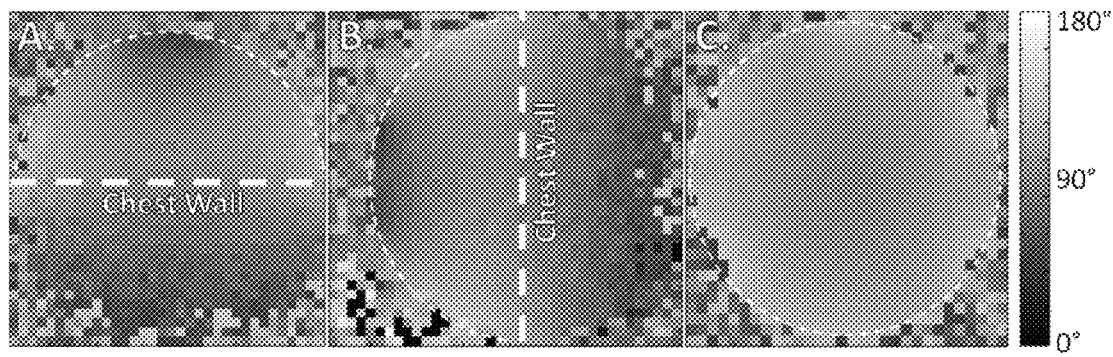
FIG. 16A    FIG. 16B    FIG. 16C
FIG. 17A    FIG. 17B    FIG. 17C
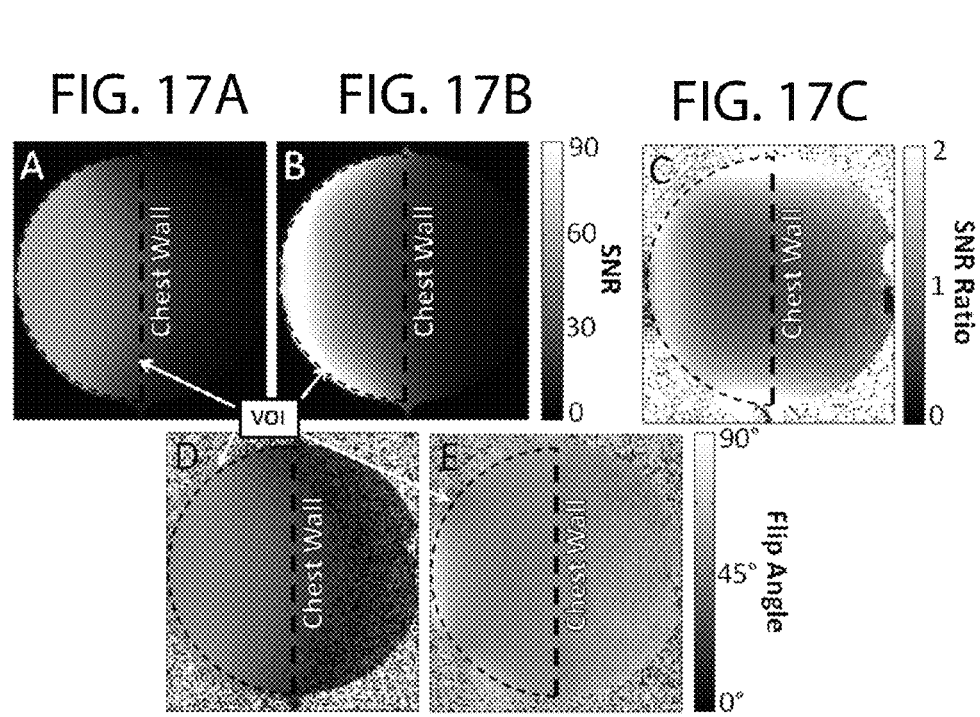
FIG. 17D    FIG. 17E

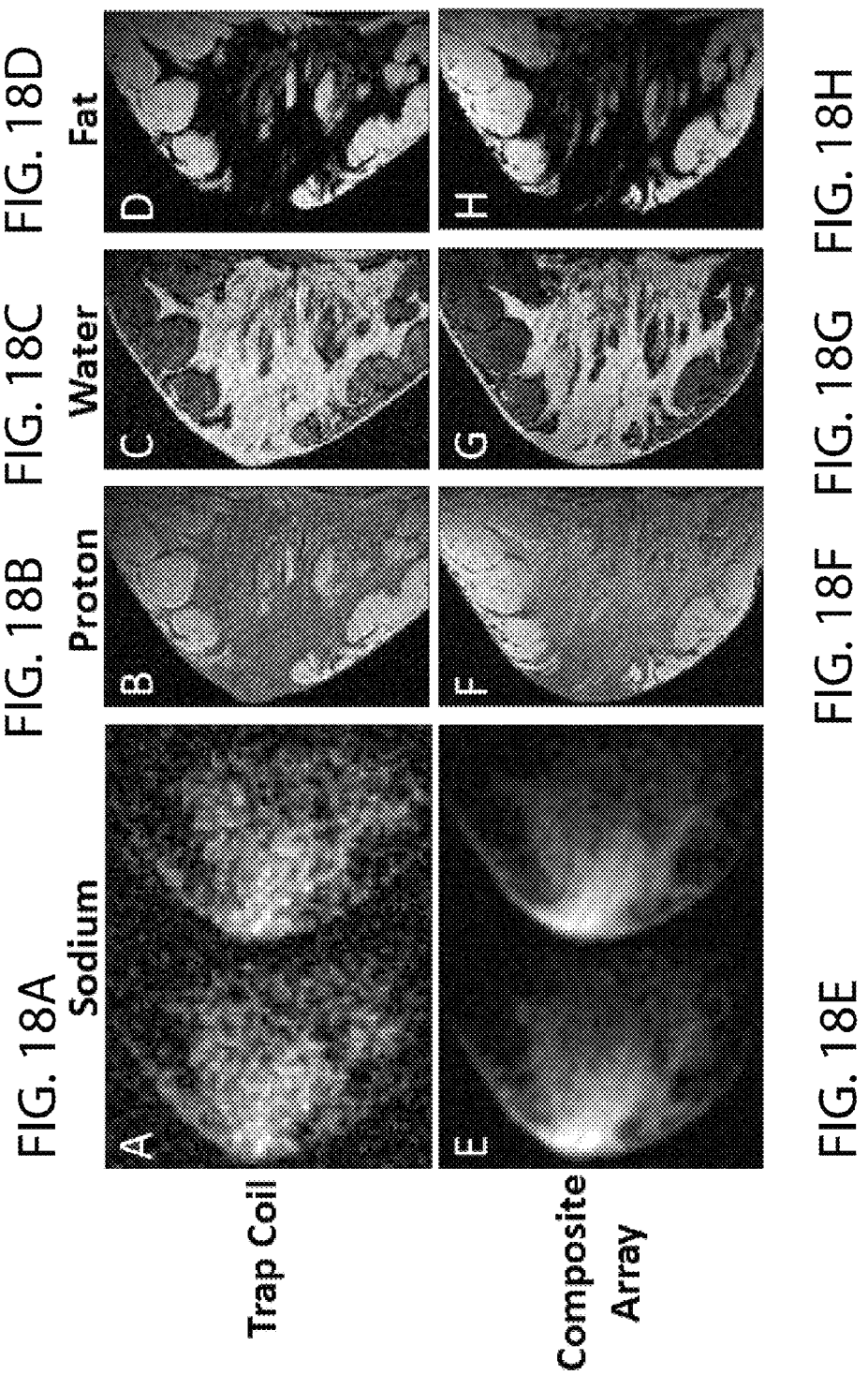

3T SODIUM AND PROTON COMPOSITE ARRAY FOR MAGNETIC RESONANCE IMAGING

CROSS-REFERENCES TO RELATED APPLICATIONS

This application claims priority as a non-provisional perfection of prior filed U.S. Provisional Application No. 61/809,163, filed Apr. 5, 2013, and incorporates the same by reference herein in its entirety.

STATEMENT OF FEDERALLY FUNDED RESEARCH

This invention was made with government support under CA112449 and DC011497 awarded by the National Institutes of Health. The government has certain rights in the invention.

FIELD OF THE INVENTION

The present invention relates to the field of radiography and more particularly relates to an improved apparatus for magnetic resonance imaging.

BACKGROUND OF THE INVENTION

Cancer is responsible for a quarter of all deaths in the United States. Breast cancer is projected to cause 458,000 deaths with 1,383,000 new cases worldwide in 2012. Breast cancer is also estimated to include 29% of all new cancer cases in women in the United States during 2012, resulting in 14% of cancer related deaths. Early detection and improved treatment have increased breast cancer survival rates in the United States over the past two decades. While proton ($^1$H) magnetic resonance imaging (MRI) is used for cancer detection due to its improved sensitivity when compared to mammography and ultrasound, $^1$H-MRI suffers from intermediate specificity which can result in false positive studies leading to unnecessary interventions. Because sodium ($^{23}$Na) concentration is known to increase in malignant lesions when compared to surrounding healthy tissues, $^{23}$Na-MRI may be able to improve specificity, potentially improving evaluation and assessment of breast lesions. Sodium MRI shows promise in characterizing and assessing tumor viability, cartilage health, renal failure, tissue damage following stroke, and multiple sclerosis. However, in comparison with conventional $^1$H-MRI, $^{23}$Na-MRI is challenging due to relatively low $^{23}$Na concentrations in biological tissues, rapid bi-exponential signal decay, and a low gyromagnetic ratio. Despite these challenges, recent improvements in coil and gradient hardware, the availability of whole-body scanners with high polarizing field strengths, and the development of more efficient pulse sequences have spurred renewed interest in $^{23}$Na-MRI. These advances have enabled the acquisition of higher quality in vivo $^{23}$Na-MRI images than previously possible, often within clinically reasonable scan times. While $^{23}$Na-MRI has become more promising, there is still a need for improved image quality and signal-to-noise ratio (SNR) to make quantitative $^{23}$Na-MRI feasible for many of the clinical applications under consideration.

Phased array coils can be used to improve the SNR of $^{23}$Na-MRI. This is achieved through simultaneous data acquisition from multiple surface coils which have inherently increased signal sensitivity and limited noise volume by being placed in close proximity to the object or anatomy of interest. Specifically designed coil arrays also allow reductions in image acquisition time through the application of parallel imaging techniques. Phased array coil concepts have been extensively applied to $^1$H-MRI coil design, routinely providing improved SNR and accelerated image acquisition compared to that provided by volume coils or other large coils of similar area. However, phased arrays have not been widely used in non-proton imaging, and typically require sophisticated custom hardware for implementation on commercial scanners. Despite these challenges, sites with the capability to support multi-channel non-proton receivers are becoming increasingly common. The first reported non-proton phased array was built for phosphorous imaging in 1992 almost a decade before the first reported $^{23}$Na array at 1.5T in 2000. In the past few years, there has been a substantial increase in the number of $^{23}$Na coil arrays developed for 3T, 4T, and 7T. Some of these array configurations are dual resonant, with the ability to image $^1$H and $^{23}$Na without repositioning the subject The preferred embodiment of the present invention is a new dual resonant breast coil design consisting of a 7-channel $^{23}$Na receive array, a larger $^{23}$Na transmit coil, and a 4-channel $^1$H transceive array. The new composite array design utilizes smaller $^{23}$Na receive loops than those typically used in $^{23}$Na imaging. Novel methods are also employed to decouple the receive loops from the transmit loops. A novel multi-channel $^1$H transceive coil is superimposed on the $^{23}$Na receive array, and decoupling between $^1$H and $^{23}$Na elements is achieved by intersecting the constituent loops to reduce the mutual inductance between the $^1$H and $^{23}$Na arrays. The new design achieves excellent $^{23}$Na-SNR over the sensitive volume while also providing good image quality for conventional $^1$H imaging.

The present invention represents a departure from the prior art in that the MRI coil design of the present invention allows for smaller and more efficient receive loops and a decoupling methodology allowing for good imagery of desired tissues in a shorter period of time for image acquisition. The preferred embodiment in this Specification is a breast coil used to diagnose and locate cancerous lesions in human breast tissue; however, it is to be understood that the concepts and details of the invention may be adapted to create scanning apparatuses and structures for use with any individual component of targeted anatomy. As such, while described in terms of a breast coil, the invention should be understood to include other structures and constructions which may be specific to a desired portion of anatomy other than the human breast.

SUMMARY OF THE INVENTION

In view of the foregoing disadvantages inherent in the known types of MRI techniques and apparatuses, this invention provides an array of transmit and receive coils capable of generating proton and sodium imagery within acceptable periods of time for accurate diagnosis and location of cancerous lesions. As such, the present invention's general purpose is to provide a new and improved MRI array that is compact, efficient to operate and capable of improving both resolution of MRI as well as time necessary to accomplish an MRI scan.

To accomplish these objectives, the composite array design consists of a hemispherical fiberglass former with seven $^{23}$Na receive loops, four $^1$H transceive loops, and a single circular $^{23}$Na transmit loop that surrounds the perimeter of the coil. A patient friendly support structure is used to position the coil and subject. Decoupling of the loops is accomplished using forward DC biased crossed diode pairs The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 15 is a series of phantom sodium SNR maps of the central (I) sagittal and (II) axial slices using the (A) composite array and (B) trap coil. FIG. 15C depicts the ratio of the composite array to trap coil SNRs. FIG. 15D is a histogram of sodium voxel SNRs obtained from the VOI within the phantom comparing the trap coil and composite array.

FIG. 16 is a series of flip angle maps of central slices from the composite array taken in a phantom study, being the (A) Axial, (B) sagittal, and (C) coronal sodium transmit flip angle maps.

FIG. 17 is a series of proton SNR maps of the central sagittal slice in a phantom study of the invention using the (A) prior art trap coil and (B) composite array. FIG. 17C depicts the ratio of the composite array to trap coil SNRs while FIGS. 17D and 17E depict flip angle maps of the trap coil and composite array, respectively.

FIG. 18 is a series of in vivo breast images of a normal volunteer showing (A,E) sodium, (B,F) proton, (C,G) water, and (D,H) fat obtained using the prior art trap coil (A-D) and composite array (E-H).

DETAILED DESCRIPTION OF THE PREFERRED EMBODIMENT

With reference now to the drawings, the preferred embodiment of the composite array is herein described. It should be noted that the articles "a", "an", and "the", as used in this specification, include plural referents unless the content clearly dictates otherwise.

$^{23}$Na Receive Array:

Prior to construction of the $^{23}$Na receive array, multiple 65 mm diameter loops were tested with different gauge copper wires and capacitor positions. Wire thicker than 14 AWG was not considered feasible for a receive array with small loops, due to the difficulty of using very thick wire for coil construction. The quality factors (Q) of these loops were measured using two stationary decoupled magnetic field probes when the coil was unloaded and loaded (Table 1). The highest Q-ratios were measured using 14 AWG and 16 AWG wire with two capacitors per loop (Table 1). Because these values were similar, the receive array was constructed using 16 AWG wire for its increased ease of use when overlapping the coils on the hemispherical former.

TABLE 1

| Thickness (AWG) | # Capacitor segments | Cap. value per segment (pF) | $Q_{unloaded}$ | $Q_{loaded}$ | $Q_{ratio}$ |
|---|---|---|---|---|---|
| 20 (thin) | 3 | 391 | 222 | 161 | 1.38 |
| 20 | 2 | 268 | 213 | 160 | 1.33 |
| 16 | 3 | 465 | 263 | 179 | 1.47 |
| 16 | 2 | 295 | 282 | 187 | 1.51 |
| 14 | 3 | 465 | 254 | 176 | 1.48 |
| 14 (thick) | 2 | 327 | 264 | 176 | 1.50 |

Figure 1:
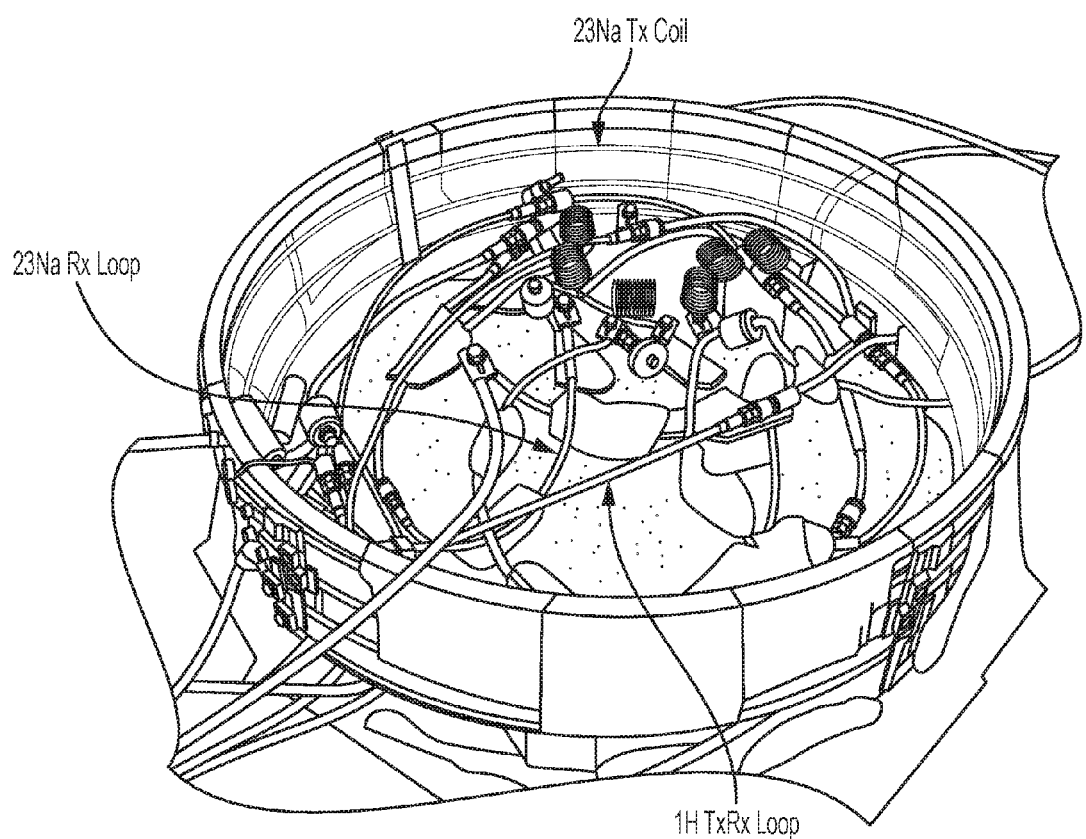
FIG. 1 is a picture of a 23Na/1H dual resonant multi-channel composite array.
Figure 2:
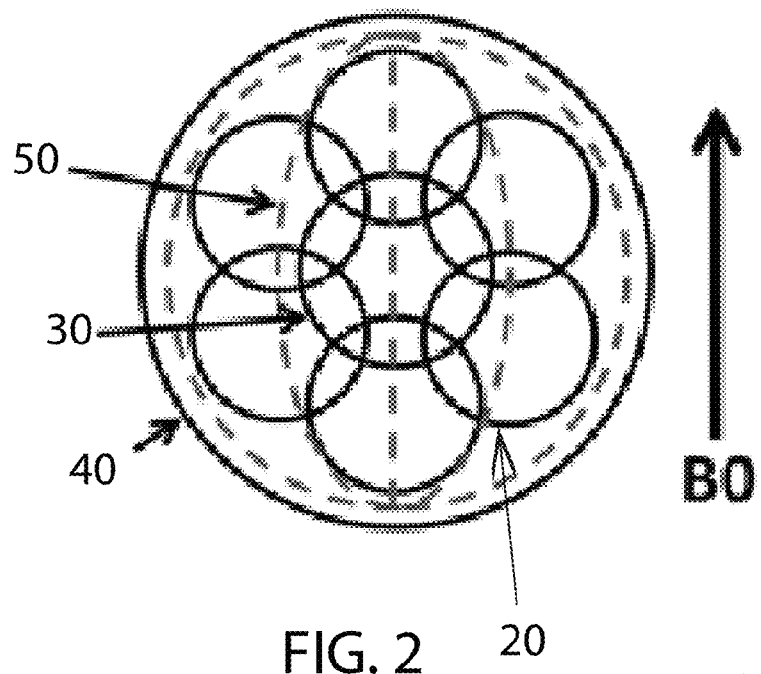
FIG. 2 is a top view schematic of the composite array coil layout, the proton coil layout is dashed. The sodium loops are solid.
Figure 3:
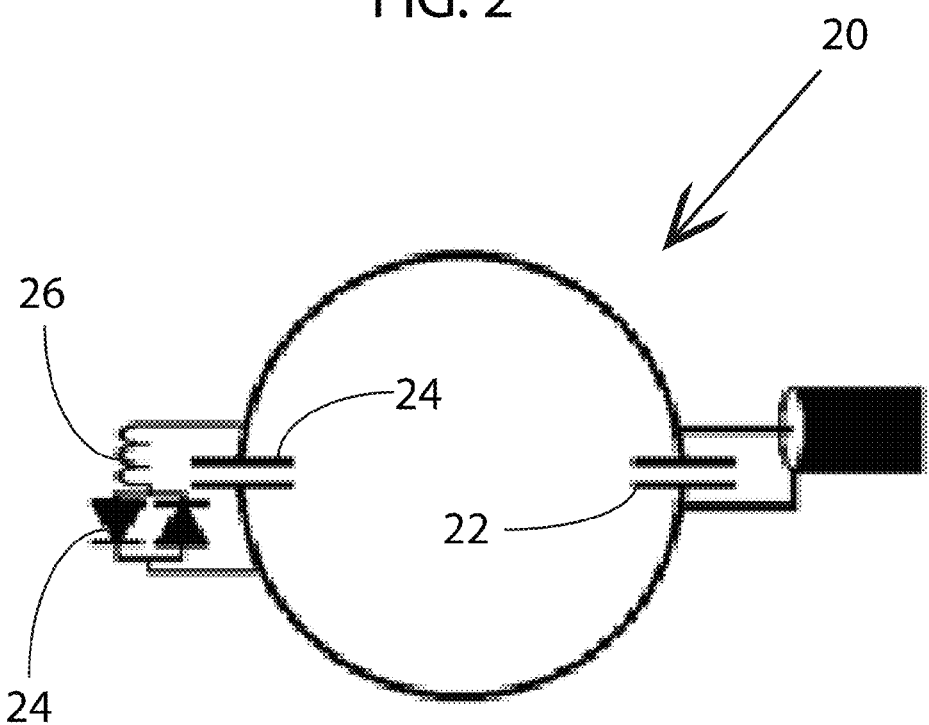
FIG. 3 is a circuit diagram of the 23Na receive loops.

Seven 16 AWG circular $^{23}$Na receive loops are positioned on a hemispherical fiberglass former (FIG. 1). Six of the loops 20 are 65 mm in diameter, and surround a single 75 mm diameter loop 30 placed at the top of the hemisphere (FIG. 2). Each loop is positioned for appropriate overlap decoupling. A loaded isolation (S21) of −18 dB is achieved between adjacent coils without preamplifier decoupling. The change in any receive coil sensitivity while loaded, measured with two decoupled magnetic probes with and without preamplifiers, has been measured at 15 dB. Each loop incorporates a matching 22 and a tuning 24 capacitor, with combined active/passive $^{23}$Na decoupling circuitry positioned at the tuning capacitor location (FIG. 3). The ideal capacitor values are approximately 180 pF and 1000 pF for tune and match respectively. The change in loop sensitivity between resonant and detuned states is greater than 45 dB when loaded. The maximum and average off diagonal noise correlation coefficient was 0.54 and 0.37, respectively.

Figure 7:
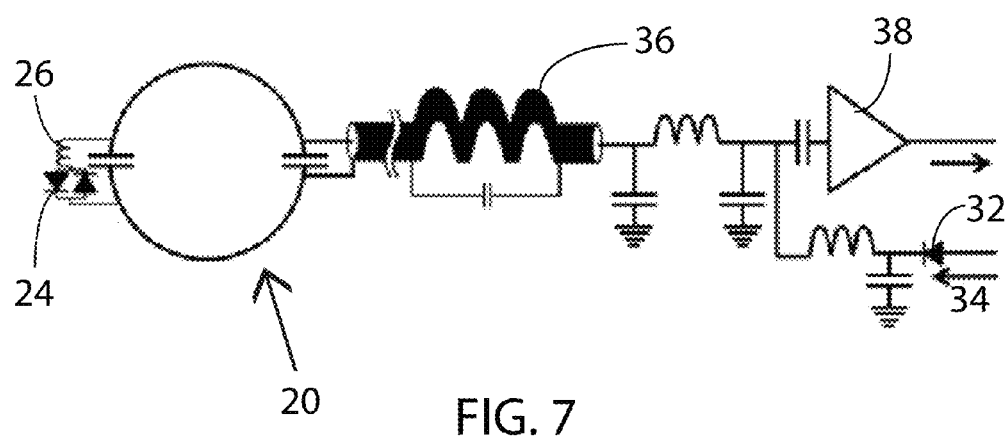
FIG. 7 is a circuit diagram of the 23Na receive loops and hardware.

Combined active/passive decoupling is achieved by placing a crossed diode pair 26 (MA4P7464F-1072T, Macom, Lowell, Mass., USA) in series with an inductor 28 that is resonant with the tune capacitor when forward-biased (FIG. 3). The loops remain resonant during receive when the diodes are not biased. Each loop is connected to an independent DC bias line 34 that provides the 100 mA/10 VDC or −30 VDC bias current. To avoid biasing the crossed diodes with the negative DC bias, a single diode 32 is added into the bias line so that only positive DC current can be supplied to the loops (FIG. 7). During trials, the active/passive trap was forward-biased during 23Na transmit, detuning the receive loops. The phase shifter completed a half-wave phase shift between the coil and preamp for preamp decoupling of the loop during the receive portion of the pulse sequence. By eliminating the negative DC voltage at the loop, the crossed diodes are not activated during receive. Passive $^1$H traps are not used in the $^{23}$Na receive loops because they would increase coil resistance, reducing sensitivity. Unfortunately, the match/tune capacitor values are too large to implement active $^1$H decoupling across those capacitors so no active $^1$H decoupling is implemented in the $^{23}$Na loops. Larger coils or decreased wire thickness could be used to decrease the capacitor values (Table 1); however, this would likely result in reduced $^{23}$Na receive sensitivity and the capacitor values would still be too large to implement effective active $^1$H-decoupling.

Each receive loop 20 is attached to a 60 cm coaxial cable 36 (<1/10 of the NMR signal wavelength for $^{23}$Na at 3T in the coaxial cable). The long coaxial cable 36 allows the receive circuitry to be placed in a convenient location for patient positioning and comfort. A $^{23}$Na trap on the coaxial cable shield is used to reduce common mode currents in the long cables, and a phase shifter circuit is used to obtain a 180-degree phase shift between the coil and preamplifier 38 to achieve preamplifier decoupling.

Figure 4:
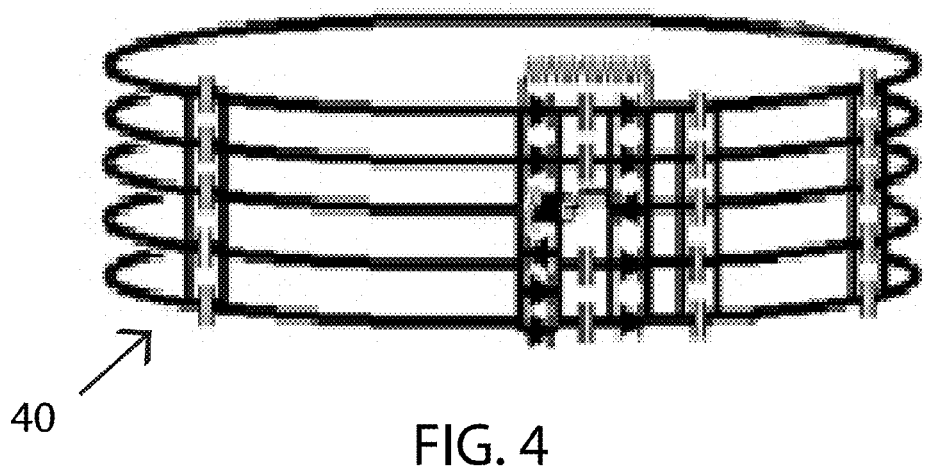
FIG. 4 is a schematic of the single channel 23Na transmit coil.
Figure 5:
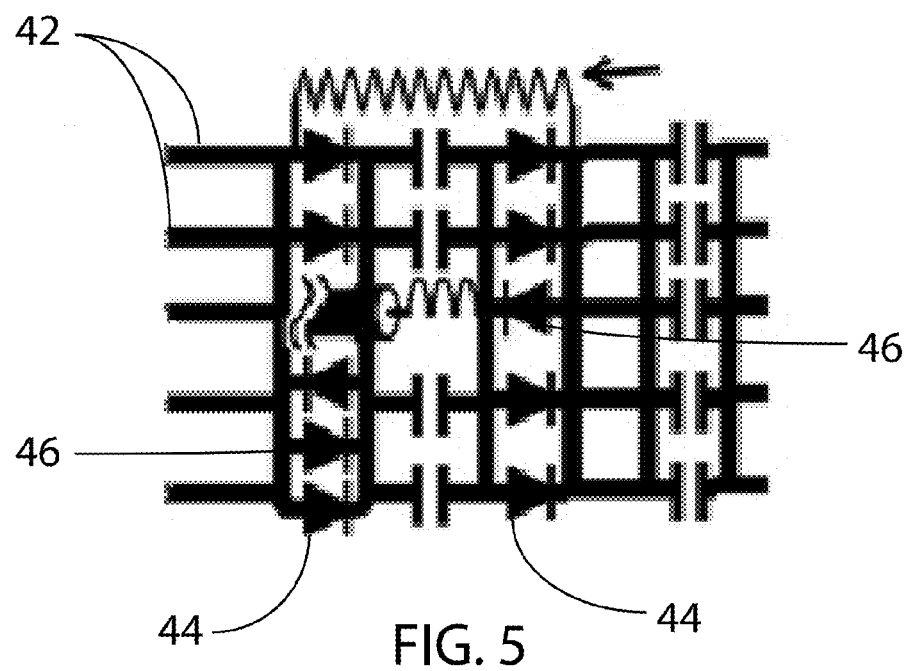
FIG. 5 is an enlarged view of the decoupling circuitry for the transmit coil of FIG. 4.

$^{23}$Na Transmit Coil:

The $^{23}$Na transmit coil 40 (FIG. 2) consists of five co-axial copper loops 42 equally spaced on a 57 mm tall, 178 mm diameter acrylic tube (FIGS. 4, 5). The loops are connected at their capacitors, making the transmit coil behave like a single-turn solenoid (FIGS. 4, 5). The capacitors are distributed along the height of the coil to help evenly distribute the current on the cylinder of the coil. The transmit coil was tuned inside a large copper shield that simulated the RF shield in the bore of the scanner. Decoupling is achieved by breaking the RF current path with serial diodes 44 in two positions. At each of these two positions, four diodes 44 are placed in parallel, equally spaced along the acrylic tube to distribute current along the height of the coil. The coil is designed so that it is resonant when forward-biased with +100 mA and detuned when unbiased. When forward-biased, the coil remains tuned and the diodes remain on even when high RF transmit power is used (up to many kilowatts). As shown in FIG. 5, a fifth diode 46 may be placed antiparallel to the original four diodes to protect them from large reverse bias voltages that can occur during transmit resulting in permanent diode breakdown if not properly forward-biased. In studies with the preferred embodiment of this invention, loaded isolation between the detuned transmit coil and resonant receive coils was measured to be −39 dB while loaded isolation between the tuned transmit coil and detuned receive coils was −42 dB.

Figure 12:
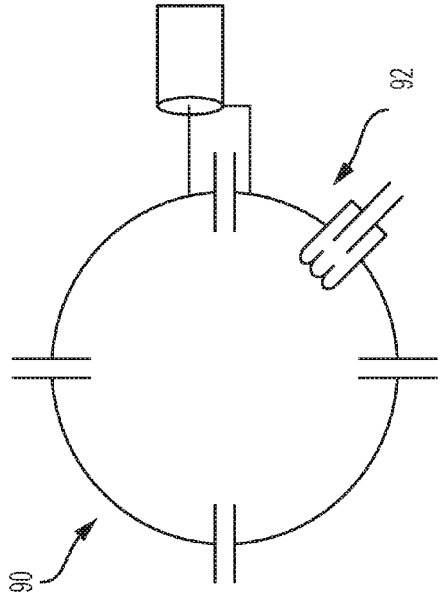
FIG. 12 is a chart showing measurement of Q-ratio are plotted for different in-plane center-to-center coil distances for a 65 mm diameter proton (dashed) and sodium (solid) loop that overlap each other.

$^1$H Transceive Array:

The inherent drawback of many $^1$H and $^{23}$Na coil configurations is that the $^{23}$Na loops have high capacitor values when compared to the $^1$H loops, creating low impedance loops at the $^1$H frequency. The low impedance $^{23}$Na loops have a shielding effect at the $^1$H frequency, resulting in $^1$H flux blockage, which is similar to the effect of a solid conducting copper loop. When a $^{23}$Na and $^1$H loop overlap, the $^1$H loop will be affected by the presence of the $^{23}$Na loop to a much greater degree than the $^{23}$Na loop will be affected by the presence of the $^1$H loop. When frequency shift, Q-ratio, and SNR are measured for two overlapping 65 mm diameter $^1$H and $^{23}$Na loops, the $^{23}$Na loop will have only minor changes (<1%) when a $^1$H loop is present, regardless of the in-plane center-to-center coil distance (FIGS. 12, 13) In comparison, at zero center-to-center distance the $^1$H loop frequency greatly increases (>30%) and the Q-ratio is more than halved. The shielding effects of the $^{23}$Na loops on the $^1$H signal can be reduced substantially by intersecting the $^{23}$Na loops with the $^1$H elements.

Figure 6:
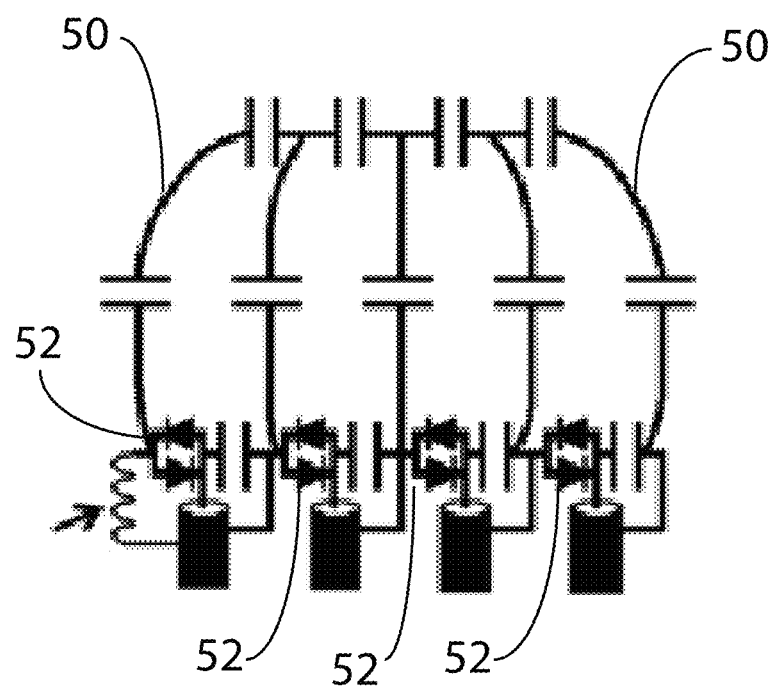
FIG. 6 is a warped schematic of the 1H transceive loops.

The composite array design employs four local $^1$H loops arranged as a ladder network, with a minimum loaded isolation between any two loops of the coil measured at 9.5 dB. The $^1$H loops 50 are positioned over the $^{23}$Na receive array such that the wire elements of the $^1$H loops bisect the $^{23}$Na loops 20, 30 (FIG. 2). The $^1$H loops are mounted 1 cm away from the fiberglass former to reduce coupling with the $^{23}$Na loops, to fit over $^{23}$Na loop circuits, and to improve $^1$H homogeneity. Each of the $^1$H transceive loops contain a crossed diode pair 52 that is forward-biased during $^1$H transceive but unbiased during $^{23}$Na transmission and reception (FIG. 6). The crossed diode pair allows easy tuning/detuning of the $^1$H loops for further decoupling between the $^1$H and $^{23}$Na loops. The minimum isolation between any $^{23}$Na receive loop and $^1$H loop when the coil was loaded was: −20 dB at the $^{23}$Na resonant frequency (32 MHz) when the $^1$H loops were tuned, −37 dB when the $^1$H loops were detuned; −41 dB at the $^1$H resonant frequency (123 MHz) when the $^1$H loops were tuned, and −75 dB when the $^1$H loops were detuned. The isolation between $^{23}$Na and $^1$H loops was unchanged regardless of whether the $^{23}$Na loops were tuned. The $^1$H loops each use quarterwave cables that, when combined with the quarterwave cable in the TR switches described below, form a half-wave phase shift between the loops and preamplifiers for optimum preamplifier decoupling.

Figure 8:
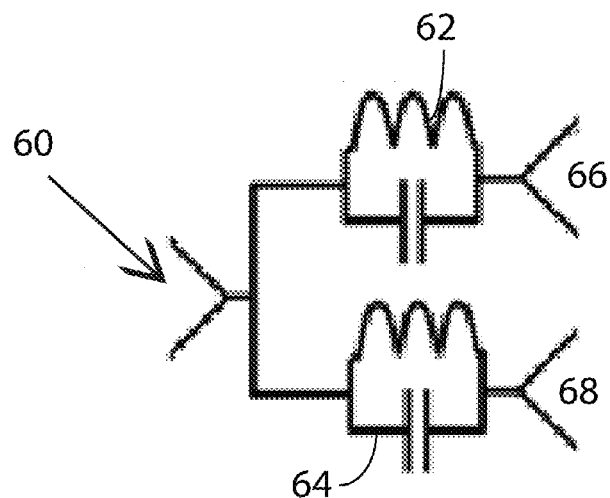
FIG. 8 is a schematic of traps used to filter the 1H and 23Na Tx RF signal measured in the system depicted in FIG. 7.
Figure 9:
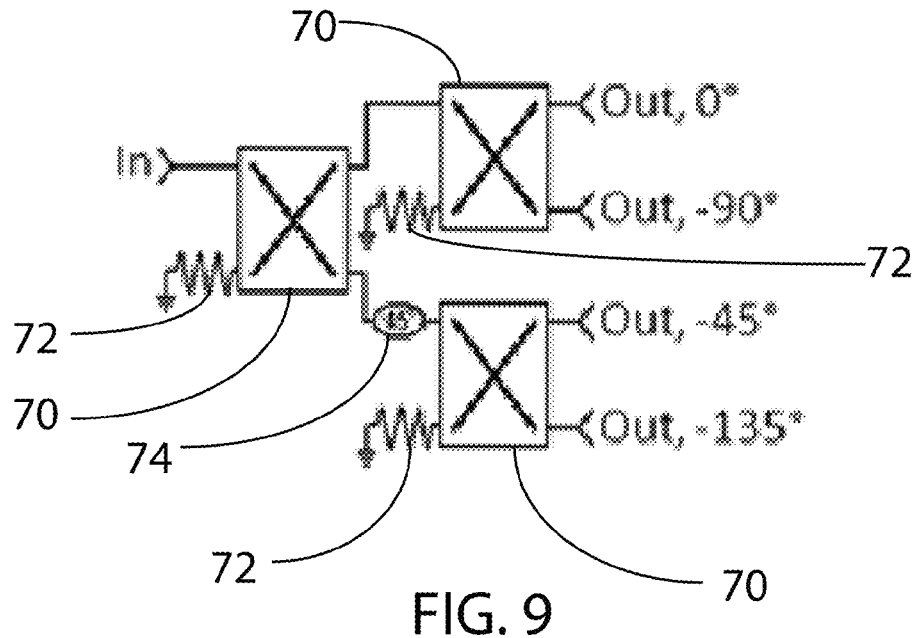
FIG. 9 is a schematic of a 1H 4-way power splitter.

Dual Resonant TR Switching:

The scanner provides a single transmit port 60 for both the $^1$H and $^{23}$Na RF transmit signal (FIG. 8). The transmit RF is passively filtered with the use of $^1$H and $^{23}$Na traps 62, 64 before going into the $^{23}$Na transmit switch 66 or $^1$H power splitter 68 (FIG. 9). The filter attenuates the $^1$H signal by −39 dB on the $^{23}$Na output, and the $^{23}$Na signal by −47 dB on the $^1$H output.

After the filter, the $^{23}$Na transmit signal passes through a large capacitor before arriving at the cylindrical $^{23}$Na transmit coil. A DC bias line 86 inserted between the large capacitor and transmit coil allows the transmit coil to be biased during $^{23}$Na transmit with +100 mA and unbiased during $^{23}$Na receive.

The $^1$H transmit signal is split across four different ports by using 90° hybrid couplers (1J0280-3, Anaren, East Syracuse, N.Y., NY, USA) 70 to initially divide the signal evenly in half, followed by two more hybrid couplers to divide the signal evenly between four ports (FIG. 9). Using three 90° hybrid couplers and a coaxial cable phase shifter, the transmit power is evenly split between each element of the 1H transceive array, with each element transmitting at a different phase. The isolation port of each coupler is terminated with a 50Ω resistor 72. Between the initial coupler and one of the secondary couplers, an extra cable length 74 is added to create a 45° phase shift. The four outputs of the power splitter each have equal magnitude but different phase shifts of 0°, 45°, 90°, and 135°. Each output is then connected to a $^1$H TR switch.

Figure 10:
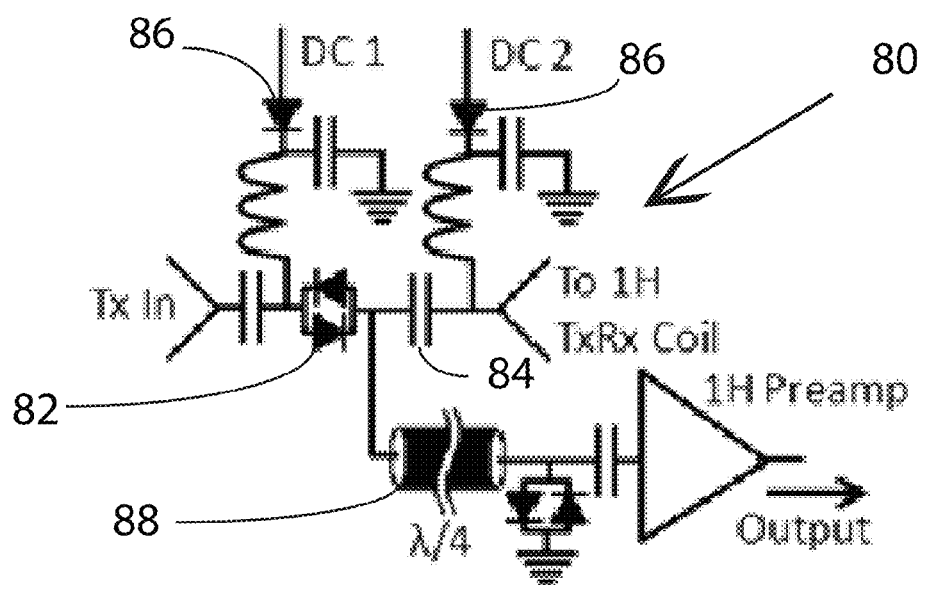
FIG. 10 is a circuit diagram of TR switches for the 1H TxRx loops where DC1 is forward-biased during 1H transmit and DC2 was forward-biased during 1H transmit and receive.
Figure 11:
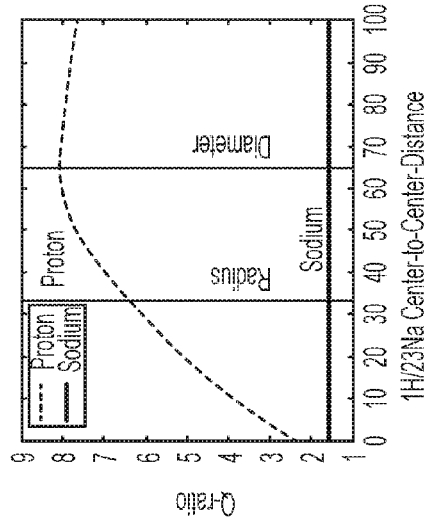
FIG. 11 is a chart showing measurement of coil frequency for different in-plane center-to-center coil distances for a 65 mm diameter proton (dashed) and sodium (solid) loop that overlap each other.

The $^1$H TR switches 80 are different from standard TR switches, in that they incorporate a reverse diode pair 82 where only a standard forward diode would typically be used, offering improved protection against incorrect DC biasing (FIG. 10). The TR switches 80 are supplied with a forward current during transmit (DC1 in FIG. 10) to activate the preamplifier protection circuitry, which consists of a quarterwave cable 88 and a diode that is shorted during transmit. A second DC line (DC2 in FIG. 10) was added between the TR switch and the loops, so that the $^1$H loops can be turned on during $^1$H transceive. Large DC blocking capacitors 84 are used to ensure that the DC bias that controls the TR switch is independent from the DC bias that controls the loops. Forward diodes 86 in may be associated with each DC line to protect against reverse bias voltages.

Figure 13:
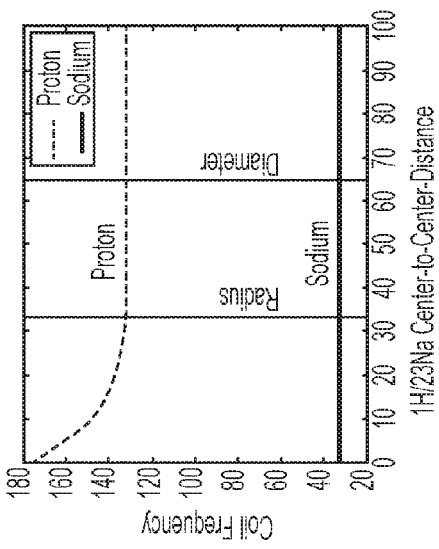
FIG. 13 is a picture of the prior art single 23Na and single 1H loop trap coil.
Figure 14:
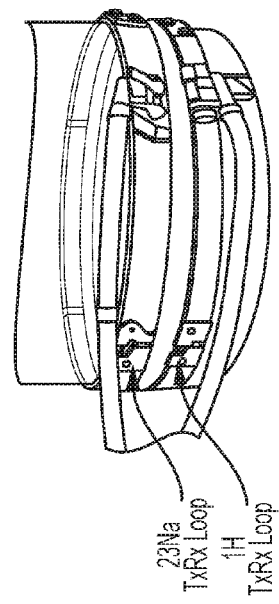
FIG. 14 is a circuit diagram of either a 23Na or 1H loop on the prior art trap coil.

23Na/1H Dual Resonant Trap Coil:

Multiple sodium breast MR studies to date have employed $^{23}$Na/$^1$H dual resonant trap coils. To gauge the performance of the composite array design, the composite array is compared to a coil 90 with a single $^1$H loop concentric with a single $^{23}$Na loop that is similar to previously used coils (FIGS. 13, 14). Both the $^1$H and $^{23}$Na loops are single-turn coils built using 10 mm wide copper tape placed on a 65 mm tall 133 mm diameter acrylic tube. The $^{23}$Na loop is positioned so that it surrounds the center of the breast with a 10 mm gap between the $^1$H and $^{23}$Na loops. The mutual inductance between the $^1$H and $^{23}$Na loops is reduced through a single passive resonant trap 92 in each coil (FIG. 14). The traps are tuned prior to insertion into the coil. When implemented, loaded isolation measured between the $^1$H and $^{23}$Na loops was −30.5 dB at $^1$H frequency and −14.5 dB at $^{23}$Na frequency. The low isolation at $^{23}$Na frequency and larger isolation at $^1$H frequency does not completely indicate the effect of each coil on each other, since the presence of the $^{23}$Na coil affects the $^1$H-SNR far more than the $^1$H coil affects the $^{23}$Na-SNR.

The trap coil was compared to a similar dual-tuned coil without traps and to single-tuned coils without traps to consider the effects of $^1$H/$^{23}$Na coil coupling at 3T. The $^{23}$Na loop on the trap coil received 80% of the SNR of the single-tuned $^{23}$Na coil. The SNR performance of the $^{23}$Na loop on the dual-tuned coil that contained no traps had no detectable difference from that of the single-tuned $^{23}$Na coil. The $^1$H loop on the trap coil had similar SNR when compared to the single-tuned $^1$H coil and received 1 to 4 times the SNR of the dual-tuned coil without traps. The primary advantage of the traps is to improve $^1$H-SNR by reducing $^{23}$Na shielding effects, despite the decreased $^{23}$Na-SNR caused by the non-zero impedance of the trap. When comparing a single resonant $^1$H loop to a $^1$H loop on a dual-tuned coil without traps, the dual-tuned coil will have similar $^1$H-SNR near the $^1$H loop but will exhibit significant reductions in SNR on the opposite side of the $^{23}$Na loop (often losing as much as 75% of the SNR).

Comparisons to the composite array were done with the trap coil design due to the trap coil's use in published $^{23}$Na breast studies. The trap coil is placed over a hemispherical fiberglass former similar to the one used with the composite array. During experiments, the coil was placed in a support structure such that the subject could lie prone, head first on the scanner table, to reduce respiratory and other motion artifacts. The support structure consists of an acrylic ramp, a flat carbon fiber board that holds the coil, and a head rest. The entire setup is padded for subject comfort during scanning.

Phantom Studies

A fast-gradient spoiled sequence using the 3D cones k-space trajectory was used to image $^{23}$Na in a 10 cm diameter spherical NaCl/CuSO$_4$ phantom. The 3D cones sequence consists of spirals that follow a cone-like trajectory, using cones of many different shapes and sizes to fill k-space for a given resolution and field-of-view (FOV). The 3D cones sequence is used to minimize image blurring and signal loss caused by the short T2* of $^{23}$Na as the trajectory achieves more efficient k-space coverage than radial acquisition trajectories and samples the signal before significant T2*decay.

Phantom studies were conducted with the composite array fully assembled. A spherical phantom with concentrations of 12 mM CuSO$_4$ and 150 mM NaCl were used. The 3D cones scan parameters were: TR/TE=50/0.27 ms, flip angle=70°, voxel size=2.5×2.5×2.5 mm, FOV=22.5 cm, cones=143, shots=1378, readout time=9.0 ms, averages=75, with a total scan time of ~1.5 hours. A long scan time was chosen to produce images of very high SNR for the phantom study. A 2D GRE sequence was used to image $^1$H with the following scan parameters: TR=1000 ms, TE=3.03 ms, flip angle=90°, voxel size=1.0×1.0×3.0 mm, FOV=250×125×3 mm, 1 average, total scan time of ~2 minutes. All scans were acquired in the sagittal plane and repeated with both the composite array and trap coil. The final SNR values of the composite array were calculated using the root sum-of-squares from images of the individual coil elements normalized by their noise. For statistical analysis of the phantom studies, the FOV was segmented into three regions: [1] a hemispherical region expected to contain the breast tissue of interest (referred to as the volume of interest, or VOI), [2] a region of background noise with no signal-yielding tissue, and [3] a signal-yielding region outside the VOI. Signal homogeneity and SNR were evaluated across the VOI.

Transmit flip angle (B1) maps of the $^1$H transceive loops were obtained using the dual angle method using a GRE sequence, with scan parameters: TR=1000 ms, TE=3.03 ms, FOV=250×125×3 mm, voxel size=1.0×1.0×3.0 mm, flip angle=45°/90°, averages=1, total scan time=4 minutes. B1 maps of the $^{23}$Na transmit coil were obtained using the phase sensitive method. Sodium B1 mapping scan parameters were: TR=100 ms, TE=15 ms, FOV=386×145×108 mm, resolution=128×48×36, voxel size=3.0 mm isotropic, averages=30, readout bandwidth=166 Hz/pixel, EPI factor=3, total scan time=58 minutes. The high number of averages used for the $^{23}$Na phantom experiment was used to achieve high SNR for the comparisons.

Human Imaging Studies

Human imaging studies were conducted after informed consent and with approval of the local institutional review board (IRB). A fast-gradient spoiled sequence using the 3D cones k-space trajectory was used for $^{23}$Na imaging in the breast of a normal volunteer, with the following scan parameters: TR/TE=40/0.27 ms, flip angle=70°, voxel size=1.25× 1.25×4 mm, FOV=22.4 cm, cones=80, shots=1078, readout time=8.2 ms, averages=20, with a total scan time of ~20 minutes. A standard $^1$H GRE acquisition was performed to compare $^1$H-SNR. The GRE scan parameters were: TR=11 ms, TE=4.7 ms, flip angle=15°, voxel size=0.90×0.90×1.2 mm, FOV=172×172×88 mm, 1 average, with a total scan time of ~3 minutes. To generate water and fat images using 3-point Dixon, the same $^1$H GRE acquisition was performed at TE=5.75 ms and TE=6.8 ms. All scans were repeated with both the composite array and trap coil. Images were acquired in the sagittal plane. The volunteer was moved when switching coils but not between $^{23}$Na and $^1$H scans. The final images were combined using root sum-of-squares of the individual coil element images with normalized noise floors.

Results of Testing with the Disclosed Embodiment

Phantom Studies $^{23}$Na-SNR Performance:

Within the VOI of the phantom, the composite array had a mean $^{23}$Na-SNR of 123±43 and the trap coil had a mean $^{23}$Na-SNR of 29±8. An image comparing the central sagittal slice shows an improvement in $^{23}$Na-SNR by a factor of five near the expected location of the nipple, and a factor of three or more across most of the remaining breast volume (FIG. 15). A histogram created from the voxels within the VOI (FIG. 15D) shows that while the spread of $^{23}$Na-SNR values is much larger using the composite array, the dramatic improvements in $^{23}$Na-SNR are also clearly evident.

$^{23}$Na Homogeneity:

Flip angle maps for $^{23}$Na excitation using the $^{23}$Na transmit and receive loops are shown in FIG. 16. Reasonable homogeneity is observed across the VOI, although some variation is observed, particularly in the center of the coil near the nipple and toward the edges of the breast.

$^1$H-SNR Performance:

The composite array had a mean $^1$H-SNR of 516±258 and the trap coil had a mean $^1$H-SNR of 409±177 within the VOI. The $^1$H-SNR in the composite array relative to the trap coil improved by roughly a factor of two near the $^1$H loops, although it decreased by 20% near the center of the breast phantom (FIG. 8A-C).

$^1$H Homogeneity:

The composite array obtains excellent homogeneity in the VOI, although there is some transmit B1 focusing near the center of the $^{23}$Na loops and transmit B1 shielding where the $^{23}$Na loops overlap (FIG. 17E). The phased array had a standard deviation that was 13% times the mean flip angle and the trap coil had a standard deviation that was 23% times the mean flip angle.

Human Imaging Studies $^{23}$Na-SNR Performance:

Sodium SNR improvements similar to those seen in the phantom study were observed in vivo in a normal human volunteer using the composite array (FIG. 18A, 18E). Regions with sodium displayed a 2-5× increase in $^{23}$Na-SNR over the single-loop trap coil design. Improved $^{23}$Na-SNR is evident with noticeably improved depiction of small anatomic features within the breast (FIG. 18E). The composite array obtains excellent $^{23}$Na-SNR over the entire VOI (FIG. 18E).

$^1$H-SNR Performance:

Both the trap coil and the composite array obtain good $^1$H images (FIG. 18 B-D,F-H). The in vivo $^1$H-SNR in the composite array was double that of the trap coil on the edges of the breast and similar in the center of the breast at the chest wall. The (C,G) water and (D,H) fat images were obtained using 3-point Dixon.

INDUSTRIAL APPLICABILITY

The composite array obtains a 2-5× increase in $^{23}$Na-SNR, which is a substantial improvement over anything that has been obtained in the past by single channel coils used in many $^{23}$Na breast studies. A 2-5× increase in $^{23}$Na-SNR translates to a 4-25× decrease in scan time for a given resolution, which can make a dramatic impact on the use of $^{23}$Na-MRI, improving the clinical feasibility of breast $^{23}$Na-MRI. The in vivo sodium breast images show a level of detail and structure not previously achieved, demonstrating imaging at a 1.25×1.25×4 mm resolution at 3T in a scan time of only 20 minutes.

The high $^{23}$Na-SNR images of the breast were obtained by using a receive array of small receive loops that are well decoupled from a large, homogeneous transmit coil during both transmit and receive. Although the Q-ratios of the $^{23}$Na composite array receive loops (Q-ratio=1.5) would typically be considered low, the loops were still very effective in improving $^{23}$Na-SNR.

Superimposing and intersecting the $^1$H loops with $^{23}$Na loops in this array design preserves the high SNR of the $^{23}$Na receive array while achieving acceptable $^1$H image quality. While the composite array has some $^1$H transmit inhomogeneities due to the presence of the $^{23}$Na receive array, the sensitive volume is reasonably homogeneous (FIG. 8E). Although not presented in the paper, when the scanner's body coil or a smaller 135 mm circular coil was used to image $^1$H with the $^{23}$Na receive array in place, the $^1$H images contained signal focusing and signal voids worse than those shown on the $^1$H-B1 maps of the composite array. A larger $^1$H transmit array will not be more homogeneous, since most of the inhomogeneity arises from the shielding effects of the $^{23}$Na loops. A $^1$H ladder coil with more elements should also be investigated as this should improve $^1$H-SNR due to the smaller $^1$H elements; however, the $^1$H-SNR is currently sufficient for standard $^1$H-MRI evaluation of breast lesions.

Further improvements to $^{23}$Na-MRI using the composite array are still possible. Some improvements include: shorter cables between the receive loops and preamplifiers, resulting in reduced cable interactions with the $^1$H signal; improving preamplifier decoupling; and, fiberglass formers that conform better to different breast sizes and shapes. It is uncertain whether the decrease in the transmit $^{23}$Na-B1 near the nipple results from the decoupling circuits (FIG. 7). If from the decoupling circuits, placing the decoupling circuits at any other location where less $^{23}$Na-SNR is obtained may not be desirable. Better $^{23}$Na image quality could likely be obtained using a more optimal multi-coil image reconstruction with noise de-correlation.

Future work will explore whether higher $^{23}$Na resolution can improve detection and evaluation of breast cancer in vivo. The improvements in $^{23}$Na-SNR will allow better $^{23}$Na T1 and T2* measurements for the evaluation of lesions, although quantitation of sodium concentrations is still desirable. The experiments in this study did not demonstrate the accuracy with which quantitative measurements of $^{23}$Na concentration could be obtained. The low Q-ratios of the $^{23}$Na loops suggest that the loops are relatively insensitive to changes in loading, so that field profiles obtained with a phantom may potentially be used for accurate quantitation. If necessary, a $^{23}$Na transmit flip angle map could be acquired within a few minutes for transmit field correction. Receive field profiles could potentially be corrected using sensitivity encoding (SENSE) reconstruction techniques that use the central regions of k-space to estimate coil sensitivities.

The described breast coil is unilateral. However, implementation of a bilateral $^{23}$Na receive array for simultaneous imaging of both breasts would be relatively straightforward. Due to the small diameters of the $^{23}$Na loops, the separation between the left and right coil receive elements is expected to be sufficient to avoid any significant loss in performance of a bilateral design vs. the demonstrated unilateral design. Bilateral sodium breast imaging is feasible without additional loss in scan time due to the large number of averages typically performed in $^{23}$Na imaging. Increasing the FOV has the same SNR advantage as signal averaging, so in any scenario in which signal averaging is needed, the FOV can be increased without a scan time penalty. For instance, doubling the imaging FOV and reducing the number of averages by a factor of two does not change scan time, resolution, or SNR efficiency.

Dual-tuned coil designs such as that described could potentially enable interleaved or even simultaneous imaging of multiple nuclei as recently demonstrated in. These kinds of schemes, while decreasing flexibility in the choice of resolution and scan parameters, could potentially provide additional multi-nuclear image data to complement $^1$H image data without a significant scan time penalty. This composite array system makes simultaneous/interleaved multi-nuclear acquisition even more attractive due to the high SNR and increased level of information that could be obtained from the $^{23}$Na images.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A composite $^1$H and $^{23}$Na array for magnetic resonance imagery, the array comprising:
   a. a plurality of $^{23}$Na receive loops formed into a $^{23}$Na receive array;
   b. a $^{23}$Na transmit coil comprising a plurality of co-axial $^{23}$Na loops, wherein the plurality of $^{23}$Na loops surround a common central axis and are spaced apart relative to a height of the $^{23}$Na transmit coil, each $^{23}$Na loop having at least one capacitor and being electrically connected to adjacent $^{23}$Na loops of the $^{23}$Na transmit coil;
   c. at least one $^1$H transceive array, wherein each $^1$H transceive array comprises a plurality of overlapping $^1$H loops, and wherein each $^1$H loop incorporates a crossed diode pair; and
   d. a plurality of $^1$H TR switches, each switch incorporating at least one crossed diode pair,
   wherein the crossed diode pairs of the $^1$H transceive array and plurality of $^1$H TR switches are forward biased during a $^1$H transceive operation and unbiased during $^{23}$Na transmission and reception.

2. The composite array of claim 1, wherein each $^1$H transceive array comprises at least four $^1$H loops.

3. The composite array of claim 1, wherein the $^1$H loops of each $^1$H transceive array comprise wire elements that overlap the $^{23}$Na loops, thereby reducing $^1$H and $^{23}$Na coupling.

4. The composite array of claim 1, further comprising at least one forward diode positioned to serve as a buffer, that removes negative DC bias.

5. The composite array of claim 1, wherein the $^1$H loops in each $^1$H transceive array are arranged as a ladder network.

6. The composite array of claim 1, wherein the $^1$H loops of each $^1$H transceiver array comprise copper.

7. The composite array of claim 1, wherein the composite array has a hemispherical shape.

8. The composite array of claim 7, wherein the composite array is configured to receive a portion of breast of a patient.

9. The composite array of claim 1, wherein the $^{23}$Na receive loops of the $^{23}$Na receive array have a thickness ranging from 14 AWG to 20 AWG.

10. The composite array of claim 1, wherein the $^{23}$Na loops of the $^{23}$Na transmit coil are electrically connected to one another at their capacitors.

11. A composite $^1$H and $^{23}$Na array for magnetic resonance imagery, the array comprising:
   a. a plurality of $^{23}$Na receive loops formed into a $^{23}$Na receive array;
   b. a $^{23}$Na transmit coil comprising a plurality of co-axial $^{23}$Na loops, wherein the plurality of $^{23}$Na loops surround a common central axis and are spaced apart relative to a height of the $^{23}$Na transmit coil, each $^{23}$Na loop having at least one capacitor and being electrically connected to adjacent $^{23}$Na loops of the $^{23}$Na transmit coil;
   c. at least one $^1$H transceive array, wherein each $^1$H transceive array comprises a plurality of overlapping $^1$H loops, and wherein each $^1$H loop incorporates a crossed diode pair,
   wherein the plurality of $^1$H loops overlap the $^{23}$Na loops, thereby reducing $^1$H and $^{23}$Na coupling, and
   wherein the composite array has a hemispherical shape and is configured to receive a portion of a breast of a patient.

12. The composite array of claim 11, wherein each $^1$H transceive array comprises at least four $^1$H loops.

13. The composite array of claim 11, further comprising at least one forward diode positioned to serve as a buffer that removes negative DC bias.

14. The composite array of claim 11, wherein the $^1$H loops in each $^1$H transceive array are arranged as a ladder network.

15. The composite array of claim 11, wherein the $^1$H loops of each $^1$H transceiver array comprise copper.

16. The composite array of claim 11, wherein the $^{23}$Na receive loops of the $^{23}$Na receive array have a thickness ranging from 14 AWG to 20 AWG.

17. The composite array of claim 11, wherein the $^{23}$Na loops of the $^{23}$Na transmit coil are electrically connected to one another at their capacitors.

* * * * *